Figure 1:
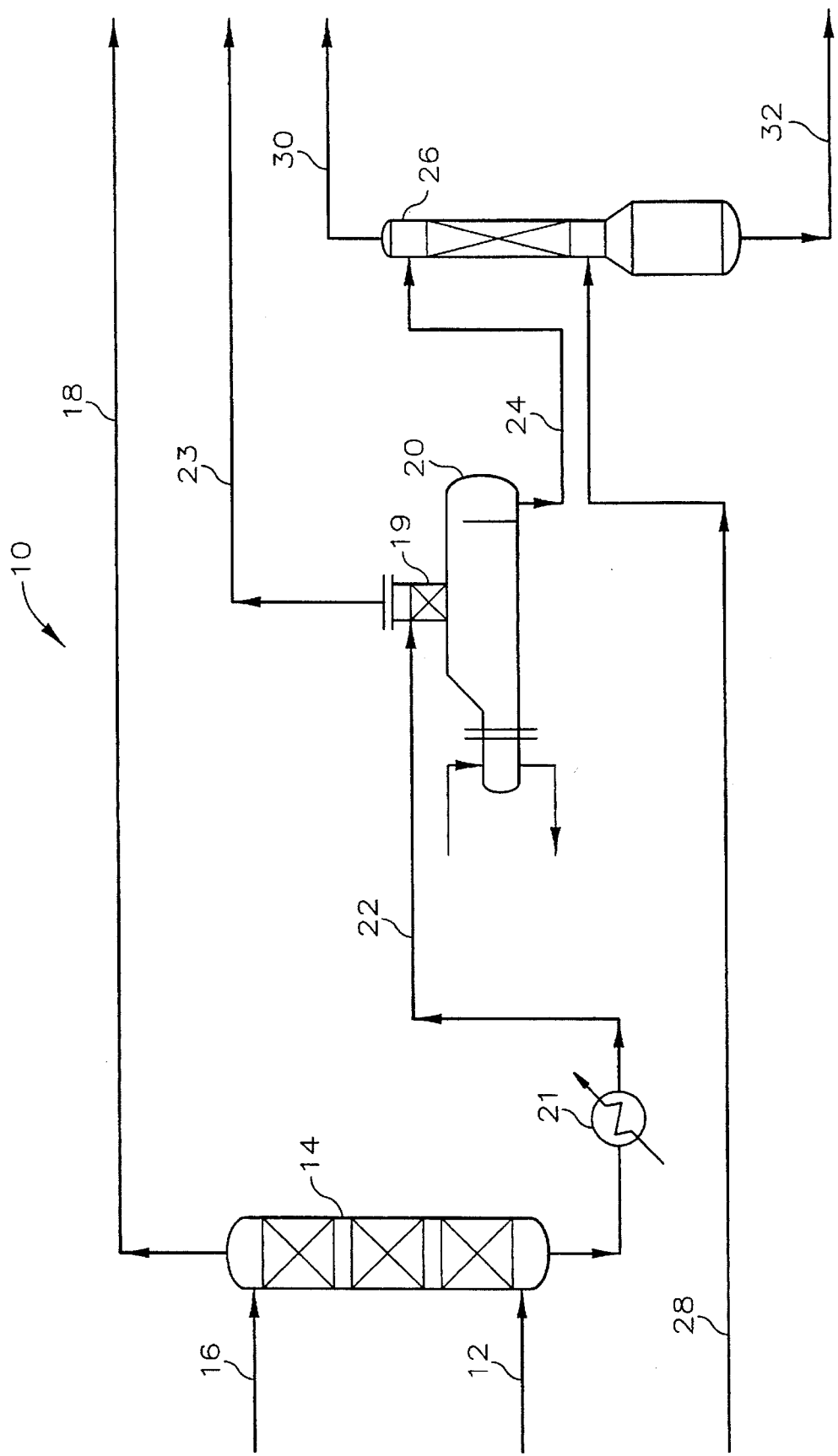

United States Patent [19]

Hovis et al.

[11] Patent Number: 5,648,587

[45] Date of Patent: Jul. 15, 1997

[54] METHOD FOR SEPARATING SULFONE FROM A HYDROCARBON STREAM HAVING A CONCENTRATION OF SULFONE PRODUCING A DRY SULFONE PRODUCT

[75] Inventors: Keith W. Hovis; Richard L. Anderson, both of Bartlesville, Okla.

[73] Assignee: Phillips Petroleum Company, Bartlesville, Okla.

[21] Appl. No.: 567,010

[22] Filed: Dec. 4, 1995

[51] Int. Cl.$^6$ .................................. C07C 2/62; C07C 7/10
[52] U.S. Cl. .................. 585/724; 585/802; 585/723; 585/857
[58] Field of Search .................. 585/724, 723, 585/802, 857

[56] References Cited

U.S. PATENT DOCUMENTS

| | | | |
|---|---|---|---|
| 3,338,823 | 8/1967 | Voetter | 208/313 |
| 3,340,185 | 9/1967 | Little et al. | 208/321 |
| 3,537,984 | 11/1970 | Thompson | 208/321 |
| 5,237,122 | 8/1993 | Eastman et al. | 585/709 |
| 5,276,243 | 1/1994 | Better et al. | 585/802 |

*Primary Examiner*—Helane Myers
*Attorney, Agent, or Firm*—Charles W. Stewart

[57] ABSTRACT

Disclosed is a process for separating sulfone from a hydrocarbon stream containing a small concentration sulfone by using water as an extraction solvent. The extraction solvent, laden with the removed sulfone, is further processed to separate the extraction solvent and water to thereby produce a sulfone product suitable for reused in an alkylation process or for sale as a dry sulfone end-product.

12 Claims, 2 Drawing Sheets

METHOD FOR SEPARATING SULFONE FROM A HYDROCARBON STREAM HAVING A CONCENTRATION OF SULFONE PRODUCING A DRY SULFONE PRODUCT

The present invention relates to a process for separating sulfone from a hydrocarbon stream which contains a concentration of such sulfone and producing a dry sulfone product.

It has recently been discovered that sulfone additives can be utilized in combination with traditional hydrogen fluoride alkylation catalysts as a means for reducing the volatility of the resultant catalyst mixture. One side effect from utilizing a sulfone additive in combination with a hydrofluoric acid alkylation catalyst is that small concentrations of sulfone become dissolved in the alkylate product from a hydrofluoric acid catalyzed alkylation process. The small concentration of sulfone in the alkylate product can have a negative impact on the alkylate as a gasoline blend component. Thus, even though the concentration of sulfone is very small, it is desirable to remove such small concentrations of sulfone from an alkylate product in order to prevent its negative economic consequences on refiners who use the alkylate as a gasoline blending component.

One method for removing sulfone from an alkylate reaction product is use of water as an extraction solvent. The water extraction solvent, however, must be removed from the sulfone in order to provide for a dry, or substantially water-free, sulfone product.

It is, thus, an object of this invention to provide a method for removing sulfone that is contained in an alkylate reaction product.

It is a further object of this invention to provide a method for separating a small concentration of sulfone contained in an alkylation reaction product which contains a concentration of such sulfone.

A yet further object of this invention is to provide a method for producing a sulfone product that has a desirably low water concentration or is substantially free of water.

A still further object of this invention is to provide for the removal of sulfone from an alkylate reaction product containing a concentration of sulfone and subsequently producing a sulfone product that has a desirably low water concentration or is substantially water-free.

Thus, the process of the present invention includes separating sulfone from a hydrocarbon stream having a concentration of sulfone and producing a dry sulfone product. This process includes extracting the sulfone from the hydrocarbon stream by contacting such hydrocarbon stream with water. The water serves as an extraction solvent by extracting at least a portion of the sulfone contained in the hydrocarbon stream and providing an extract stream enriched with the sulfone and comprising water. A raffinate stream is produced having a concentration of sulfone that is smaller than the concentration of sulfone in the original hydrocarbon stream contacted with the extraction solvent. The extract stream is passed to an evaporation zone for evaporating a portion of the water therefrom to provide a vaporous solvent stream and a liquid solute stream. The vaporous solvent stream comprises water and the liquid solute stream comprises sulfone and water. Water is stripped from the liquid solute stream by utilizing a hot stripping gas within a separation zone for separating the liquid solute stream into a stripper overhead stream, which contains water and hot stripping gas, and a stripper bottoms stream, which contains sulfone and less than about 3 weight percent water.

An additional embodiment of the invention relates to a method for removing sulfone from a hydrocarbon stream, having a sulfone concentration of less than about 3 weight percent, and for producing a dry sulfone product having a concentration of less than about 3 weight percent water. The hydrocarbon stream is contacted with a water solvent. An extract stream enriched with sulfone and comprising water is recovered. Also recovered is a raffinate stream comprising a hydrocarbon having a concentration of sulfone that is below that of the sulfone concentration of the hydrocarbon stream. The extract stream is passed to an evaporation zone for evaporating a portion of the water therefrom to provide a vaporous solvent stream containing water and a liquid solute stream containing sulfone and water. Water is stripped from the liquid solute stream by utilizing a hot stripping gas within a separation zone for separating the liquid solute stream into a shipper overhead stream containing water and a shipper bottoms stream containing sulfone and less than about 3 weight percent water.

Figure 2:
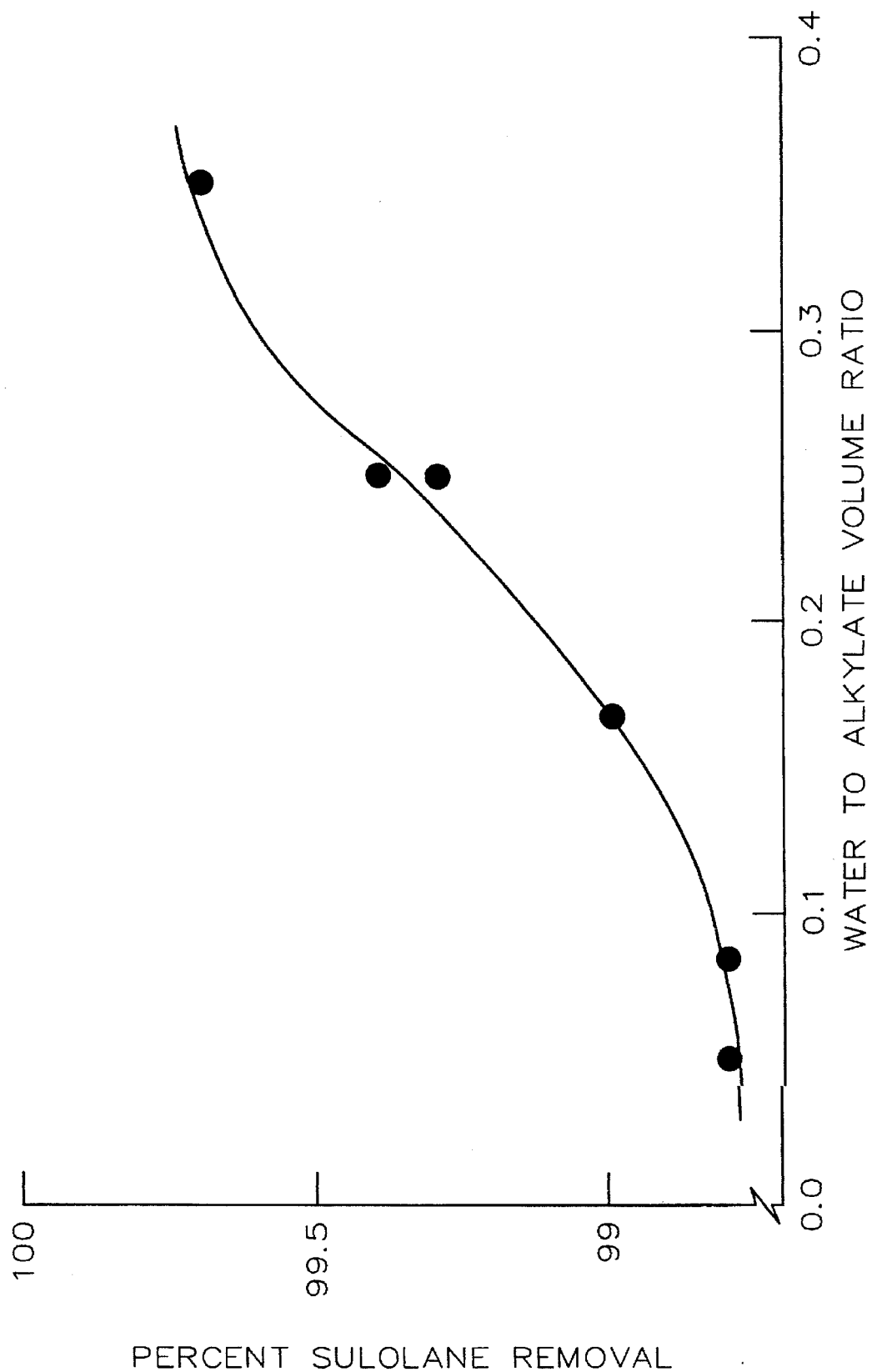

In the accompanying drawings:

FIG. 1 provides a schematic representation of the process which is one embodiment of the invention; and FIG. 2 is a plot of extraction data for water as an extractant for removing sulfolane from alkylate.

The process of this invention contemplates the resolution of problems associated with a gasoline blending component containing a small concentration of a sulfone compound. This sulfone compound, in sufficient concentrations, serves as a contaminant to a gasoline end-product when it is contained in a gasoline blending component such as an alkylate product produced by the catalytic alkylation of olefins and isoparafins. In particular, recently it has been discovered that a novel catalyst which utilizes a sulfone as one component in combination with hydrogen fluoride can provide for a suitable alkylate product. One problem, however, is that when utilizing a mixture of the hydrogen fluoride and sulfone as an alkylation catalyst, due to the slight solubility of sulfone in hydrocarbon, there is a small concentration of the sulfone that passes from the alkylation reaction system along with the alkylate end-product. It is, thus, critical that a significant portion of the sulfone contained in the alkylate end-product be removed prior to utilizing it as a gasoline blend component. The need to remove the sulfone concentration is important even though the sulfone is only slightly soluble in the alkylate hydrocarbon and that its concentration level typically will not exceed 2 or 3 weight percent of the alkylate product.

It is, therefore, important to remove a significant portion of the sulfone concentration in a hydrocarbon stream which contains such sulfone in order for the hydrocarbon stream to be useable as a gasoline blend stock. Generally, it is necessary to remove at least a portion of the sulfone from the hydrocarbon stream, which can be at least about 70 weight percent of the sulfone concentration. Preferably, it is desirable to remove at least about 80 weight percent of the sulfone contained in the hydrocarbon stream, and, most preferably, it is desirable to remove at least 90 weight percent of the sulfone concentration in the hydrocarbon stream. In fact, the novel process described herein has the exceptional ability under proper process conditions to remove at least 99 weight percent of the sulfone contained in the hydrocarbon stream when the sulfone concentration is less than about 3 weight percent.

The hydrocarbon stream of the invention generally will include hydrocarbons having from 3 to 12 carbon atoms with the most common hydrocarbons being paraffins. Specifically, the hydrocarbon stream will be an alkylate hydrocarbon product comprising paraffins produced by the catalytic reaction of olefins and isoparafins of an alkylation process. The alkylation catalyst utilized in the alkylation process comprises a sulfone component and hydrogen fluoride. The alkylation catalyst utilized in the alkylation of the olefins and isoparafins generally will have a weight ratio of hydrogen fluoride to sulfone in the range of from about 1:1 to about 40:1. A preferred weight ratio of hydrogen fluoride to sulfone in the alkylation catalyst can range from about 2.3:1 to about 19:1, and, more preferably, it can range from 3:1 to 9:1.

Alkylation processes contemplated in the present invention are those liquid phase processes wherein mono-olefin hydrocarbons such as propylene, butylenes, pentylenes, hexylenes, heptylenes, octylenes and the like are alkylated by isoparaffin hydrocarbons such as isobutane, isopentane, isohexane, isoheptane, isooctane and the like for production of high octane alkylate hydrocarbons boiling in the gasoline range and which are suitable for use in gasoline motor fuel. Preferably, isobutane is selected as the isoparaffin reactant, and the olefin reactant is selected from propylene, butylenes, pentylenes and mixtures thereof for production of an alkylate hydrocarbon product comprising a major portion of highly branched, high octane value aliphatic hydrocarbons having at least seven carbon atoms and less than ten carbon atoms.

The sulfones suitable for use in this invention are the sulfones of the general formula

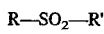

$$R-SO_2-R'$$

wherein R and R' are monovalent hydrocarbon alkyl or aryl substituents, each containing from 1 to 8 carbon atoms. Examples of such substituents include dimethylsulfone, di-n-propylsulfone, diphenylsulfone, ethylmethylsulfone and the alicyclic sulfones wherein the $SO_2$ group is bonded to a hydrocarbon ring. In such a case, R and R' are forming together a branched or unbranched hydrocarbon divalent moiety preferably containing from 3 to 12 carbon atoms. Among the latter, tetramethylenesulfone (tetrahydrothiopene-1,1-dioxide) or sulfolane, 3-methylsulfolane and 2,4-dimethylsulfolane are more particularly suitable since they offer the advantage of being liquid at process operating conditions of concern herein. These sulfones may also have substituents, particularly one or more halogen atoms, such as for example, chloromethylethylsulfone. These sulfones may advantageously be used in the form of mixtures.

Because of a slight solubility of sulfone in the alkylate hydrocarbon product, there will be a small concentration of sulfone therein. Generally, the sulfone concentration is less than about 3 weight percent of the total weight of the alkylate hydrocarbon product. More specifically, the sulfone concentration in the alkylate hydrocarbon product can range from about 0.01 weight percent to about 3 weight percent depending on processing conditions. Ordinarily, the sulfone concentration in the alkylate hydrocarbon product can range from about 0.1 weight percent to about 2 weight percent and, most likely, it can range from 0.15 weight percent to 1 weight percent.

Because of the contamination caused by an excessive concentration of sulfone in the alkylate hydrocarbon product it is desirable to remove at least a portion of the sulfone in the alkylate hydrocarbon product so as to have a gasoline blend component that can suitably be blended with other gasoline components to produce a desirable gasoline endproduct. Thus, a substantial portion of the sulfone content of the alkylate hydrocarbon product is removed by the inventive process which can be at least about 70 weight percent of the sulfone contained in the alkylate hydrocarbon product. Preferably, it is desirable to remove at least about 80 weight percent of the sulfone content of the alkylate hydrocarbon product and, most preferably, it is desirable to remove at least 90 weight percent of the sulfone content. Because of the efficiency of the process of this invention, it is even possible under appropriate process conditions to remove upwardly to 99 weight percent or more, of the sulfone contained in the hydrocarbon alkylation product.

The alkylate hydrocarbon product is contacted with an extraction solvent comprising, consisting of, or consisting essentially of, water. Any suitable contacting means for contacting the extraction solvent with the alkylate hydrocarbon product can be used for providing intimate mixing or contacting of the extraction solvent with the alkylate hydrocarbon product. Such contacting means as plate columns, packed columns or single stage contacting means, which include static mixers and mechanically agitated vessels, may be used. Thus, any means which provides for the intimate contacting or mixing of the extraction solvent with the alkylate hydrocarbon product may be used as a part of this invention.

Any amount of extraction solvent relative to the quantity of the alkylate hydrocarbon product can be utilized in the process provided the amount of extraction solvent contacted with the alkylate hydrocarbon product is effective for the removal of at least a portion of the sulfone contained in the alkylate hydrocarbon product. Generally, contacting efficiency requires an amount of extraction solvent with the alkylate hydrocarbon product such that the volumetric ratio of water contacted with the alkylate hydrocarbon is at least about 0.01:1 water to hydrocarbon. Preferably, the volumetric ratio of water contacted with hydrocarbon is at least about 0.02:1 and, most preferably, the volumetric weight ratio can exceed 0.05:1. Economics will generally set the upper limit for the volumetric ratio of water to alkylate hydrocarbon product.

An extract stream enriched with sulfone and comprising water is recovered from the contacting means. The extract stream will contain at least a portion of the sulfone contained in the alkylate hydrocarbon product and can contain, as earlier described herein, at least about 70 weight percent of the sulfone contained in such alkylate hydrocarbon product. The extract stream will generally contain upwardly to about 20 weight percent sulfone, but, specifically, the concentration range of sulfone in the extract stream will be in the range from about 0.25 weight percent to about 15 weight percent. More specifically, the sulfone concentration in the extract stream is in the range from 0.5 weight percent to 10 weight percent.

The water concentration of the extract stream generally exceeds about 80 weight percent. Specifically, the water concentration in the extract stream can be in the range from about 85 weight percent to about 99.75 weight percent. Most specifically, the water concentration can be in the range from 90 weight percent to 99.5 weight percent.

Also recovered from the contacting means is a raffinate stream comprising the alkylate hydrocarbon product and having a reduced sulfone concentration below that of the alkylate hydrocarbon product. Generally, the sulfone concentration of the raffinate stream can be less than about 300 parts per million weight (ppmw). Preferably, however, the concentration of sulfone in the raffinate stream can be less than about 100 ppmw and, most preferably, the concentration sulfone in the raffinate stream is less than 10 ppmw.

The extract stream is passed to a separation zone for separating the water from the extract stream and forming a vaporous solvent stream containing water and a liquid solute stream containing sulfone and water. Any suitable type of separation means may be used to define the separation zone but, preferably, the separation means is a conventional evaporator, which defines an evaporation zone. The evaporator provides for heat transfer and vapor-liquid separation and produces a vaporous solvent stream, containing predominantly water, and a liquid solute stream containing water and having a substantial concentration of sulfone.

Generally, the liquid solute stream from the evaporation zone can have a concentration of less than about 25 weight percent water. Preferably, the liquid solute stream can contain less than about 20 weight percent water and, most preferably, the water concentration is less than 15 weight percent. The liquid solute stream generally has a high concentration of sulfone exceeding about 75 weight percent. Preferably, the sulfone concentration in the liquid solute stream will exceed about 80 weight percent and, most preferably, it will exceed 85 weight percent.

While the liquid solute stream is rich in sulfone, it is still an unsuitable sulfone product due to the high concentration of water. In order to have a desirable sulfone product, it is important that it be substantially free of water, generally less than about 3 weight percent water. If the sulfone product is to be used as a component of an alkylation catalyst, it is preferable for it to have less than about 0.75 weight percent water, and, most preferably, the sulfone product can have less than 0.5 weight percent water. In order to obtain a sulfone product having such a low concentration of water, the liquid solute stream must be charged to a stripping zone defined by stripping means such as a stripper for stripping the water from the liquid solute stream to produce a stripper overhead stream, containing water, and a shipper bottoms stream, containing sulfone, and which is suitably dry to serve as a sulfone product or to be used as a component of an alkylation catalyst.

In order to perform the shipping operation without vacuum pressure conditions, a hot shipping gas must be utilized to provide heat energy to ship the water from the liquid solute stream. The hot shipping gas is preferably a hydrocarbon selected from the group consisting of methane, ethane, propane, and mixtures thereof. But, optionally, the hot stripping gas may also be an inert gas such as nitrogen. The hot shipping gas that is charged to the stripping zone will generally have a temperature in the range of from about 150° F. to about 400° F. but, preferably, the temperature of the hot shipping gas is in the range of from 200° F. to 300° F. The advantage to using a hot stripping gas to remove water from the sulfone, as opposed to using other types of separation methods that use high temperature separation, is that vacuum pressure operating conditions are not required and the decomposition of the sulfone compounds is minimized. In any event, the stripping gas will provide energy for separating the water from the sulfone to thereby produce a stripper bottoms stream containing dry sulfone and a stripper overhead stream containing the stripping gas and water.

The stripper is operated under substantially atmospheric conditions. But, generally, the shipper pressure can range from about atmospheric pressure to about 50 pounds per square inch gauge (psig). It is preferred to operate the shipper at as close to atmospheric pressure as possible, thus, it is preferred for the stripper to operate at a pressure in the range of from about atmospheric to about 20 psig. Most preferably, the shipper is operated at a pressure in the range from atmospheric to 10 psig.

One of the advantages to this process is the ability to easily dispose of the shipper overhead stream by passing it to either a combustion flare or a fuel system. This allows for the easy disposal of the shipper overhead stream without the need of further processing. As for the stripper bottoms stream, it has a low enough water concentration to make it suitable for sale as a sulfone product or, alternatively, for reuse as a component of the alkylation catalyst of an alkylation process system.

Referring now to FIG. 1, there is presented a schematic representation of process system 10, which depicts a liquid-liquid extraction process system utilized for the extraction of a sulfone solute from an alkylate hydrocarbon product and other separation equipment for producing a dry sulfone product. The alkylate hydrocarbon product stream, which comprises an alkylate product having a concentration of sulfone, passes by way of conduit 12 to extractor 14. Extractor 14 defines a contacting zone and provides contacting means for contacting the alkylate hydrocarbon product with an extraction solvent comprising water. The extraction solvent is introduced into extractor 14 via conduit 16. A raffinate stream, which is the alkylate hydrocarbon product stream having a substantially reduced concentration of sulfone contained therein, passes from extractor 14 by way of conduit 18.

Extractor 14 is operably connected in fluid flow communication with evaporator 20 by conduit 22. A recovered extract stream, comprising water with at least a portion of the sulfone contained in the alkylate hydrocarbon product, passes from extractor 14 to evaporator 20 by way of conduit 22. Evaporator 20 defines an evaporation zone and provides for the separation of water from the extract stream to produce a vaporous solvent stream containing water, preferably, a predominant amount of water, and a liquid solute stream rich in sulfone and containing some water. It is desirable to charge the extract stream to evaporator 20 at subcooled conditions, thus, interposed in conduit 20 is heat exchanger 21, which defines a heat transfer zone and provides for indirect heat exchange to give, if necessary, a subcooled extract stream. It is preferred for evaporator 20 to be equipped with column 19 containing therein trays or packing upon which the extract stream is fed. The use of column 19 minimizes the amount of sulfone that passes with the vaporous solvent stream and eliminates the need to have refluxing equipment.

The recovered water from the vaporous solvent stream may, if desired, be returned to extractor 14 by way of conduit 23 and used as the extraction solvent to extractor 14 or it may be passed downstream for further processing. The extract stream passes by way of conduit 24 from evaporator 20 to stripper 26. Conduit 24 is operatively connected and provides for fluid flow communication between evaporator 20 and stripper 26. Stripper 26 defines a separation zone and provides stripping means for separating the sulfone from the water contained in the liquid solute stream exiting evaporator 20.

A hot stripping gas is charged to stripper 26 by way of conduit 28. The hot stripping gas provides energy for the separation of water from the sulfone component of the liquid solute stream. Thus, a stripper overhead stream is formed, which contains water and hot stripping gas, and a stripper bottoms stream is formed, which is a dry sulfone generally containing less than 3 weight percent of water. The stripper overhead stream passes from stripper 26 by way of conduit 30 and comprises primarily water recovered from the liquid solute stream and hot stripping gas. The dry, purified sulfone product passes from stripper 26 by way of conduit 32. The recovered dry sulfone, which passes from stripper 26 by way of conduit 32, may be sold as a product or reused as a sulfone component of an alkylation catalyst of an alkylation reaction process. The stripper overhead stream recovered by way of conduit 30 can be passed to a flare or used as a fuel.

The following examples are provided to further illustrate the present invention. The examples are provided for illustration purposes only; therefore, they are not intended to be a limitation upon the invention as set out in the appended claims.

folane and the sulfolane product contains less than about 0.5 weight percent water. Over 99 weight percent of the sulfolane contained in the alkylate hydrocarbon product passed to the process system is removed therefrom.

TABLE II

Calculated Material Balance
Material Balance for Process of FIG. 1

| | Streams | | | | | | | | |
|---|---|---|---|---|---|---|---|---|---|
| | 12 Liquid | 16 Liquid | 22 Liquid | 18 Liquid | 23 Vapor | 24 Liquid | 28 Vapor | 30 Vapor | 32 Liquid |
| Temperature (°F.) | 102.3 | 100.0 | 101.7 | 101.4 | 250.8 | 278.7 | 325.0 | 147.9 | 199.6 |
| Pressure (psi) | 80.0 | 68.0 | 80.0 | 68.0 | 30.0 | 31.0 | 20.0 | 18.0 | 18.2 |
| Mass Volume Fraction | 0.0 | 0.0 | 0.0 | 0.0 | 1.0 | 0.0 | 1.0 | 1.0 | 0.0 |
| Component Flow (LB/HR) | | | | | | | | | |
| Methane | 0.0 | 0.0 | 0.0 | 0.0 | 0.0 | 0.0 | 111.5 | 111.5 | 0.0 |
| Alkylate | 101363.1 | 0.0 | 0.2 | 101362.8 | 0.2 | 0.0 | 0.0 | 0.0 | 0.0 |
| Water | 0.0 | 14590.1 | 14372.6 | 217.4 | 14354.8 | 17.9 | 0.0 | 17.4 | 0.5 |
| Sulfolane | 102.1 | 0.0 | 102.0 | 0.1 | 0.7 | 101.2 | 0.0 | 0.2 | 101.0 |
| Total | 101465.2 | 14590.1 | 144474.9 | 101580.3 | 14355.8 | 119.1 | 111.5 | 129.0 | 101.5 |

EXAMPLE I

Example I presents data obtained from extraction experiments using water as an extraction solvent for removing sulfolane from alkylate. An alkylate feed containing, on average, 1082 wppm sulfolane was charged to a commercially available one inch, stirred, York-Scheibel extractor containing approximately 8 theoretical stages. The data obtained are present in Table I and are charted in FIG. 2. As the data show, water can be an effective solvent for extracting sulfolane contained in a hydrocarbon solution. The water solvent is effective in removing more than 99 weight percent of the sulfolane contained in an alkylate. The weight percent sulfolane removed increases with increasing water to alkylate ratios.

TABLE I

| Water/Alkylate Ratio (vol/vol) | Sulfolane Removal (weight percent) | Alkylate/Water Ratio (vol/vol) |
|---|---|---|
| 0.050 | 98.8 | 20 |
| 0.083 | 98.8 | 12 |
| 0.167 | 99.0 | 6 |
| 0.250 | 99.3 | 4 |
| 0.250 | 99.4 | 4 |
| 0.330 | 99.7 | 3 |

EXAMPLE II (CALCULATED)

This calculated example illustrates the benefits achievable from the novel process as depicted by FIG. 1. Table II shows the mass flows corresponding to the numbered streams of FIG. 1. As can be seen from the material balance of Table I, the washed alkylate product contains about 1 ppmw sul- While this invention has been described in terms of the presently preferred embodiment, reasonable variations and modifications are possible by those skilled in the art. Such variations and modifications are within the scope of the described invention and the appended claims.

That which is claimed is:

1. A process for separating sulfone from a hydrocarbon stream containing a concentration of a sulfone and for providing a dry sulfone product, said process comprises:

extracting said sulfone from said hydrocarbon stream by contacting said hydrocarbon stream with water to thereby extract at least a portion of said sulfone from said hydrocarbon stream and to provide an extract stream enriched with said sulfone and comprising water and a raffinate stream having a reduced concentration of said sulfone below said concentration of said sulfone in said hydrocarbon stream;

passing said extract stream to an evaporation zone defined by evaporator means for evaporating at least a portion of the water from said extract stream to provide a vaporous solvent stream and liquid solute stream, wherein said vaporous solvent stream comprises water and said liquid solute stream comprises sulfone and water; and stripping water from said liquid solute stream by utilizing a hot stripping gas in a separation zone defined by stripping means for separating said liquid solute stream into a shipper overhead stream containing water and said hot shipping gas and a shipper bottom stream containing sulfone and less than about 3 weight percent water.

2. A process as recited in claim 1 wherein said concentration of said sulfone in said hydrocarbon stream is less than about 1 weight percent.

3. A process as recited in claim 2 wherein said at least a portion of said sulfone represents at least about 70 weight percent of said sulfone in said hydrocarbon stream.

4. A process as recited in claim 3 wherein said hydrocarbon stream comprises paraffin compounds.

5. A process as recited in claim 4 wherein said paraffin compounds include paraffins produced by the catalytic reaction of olefins and isoparafins.

6. A process as recited in claim 5 wherein said sulfone is sulfolane.

7. A process as recited in claim 6 wherein the weight ratio of water contacted with said hydrocarbon stream is at least at about 0.01:1 water to hydrocarbon.

8. A method for removing sulfone from a hydrocarbon stream having a sulfone concentration and containing a hydrocarbon and for producing a dry sulfone product, said method comprising:

contacting said hydrocarbon stream, having said sulfone concentration which is less than about 3 weight percent, with a solvent comprising water;

recovering an extract stream enriched with sulfone;

recovering a raffinate stream comprising said hydrocarbon and having a reduced sulfone concentration below said sulfone concentration;

passing said extract stream to an evaporation zone defined by evaporator means for evaporating at least a portion of the water from said extract stream to provide a vaporous solvent stream containing water and a liquid solute stream containing sulfone and water; and stripping water from said liquid solute stream by utilizing a hot stripping gas in a separation zone defined by stripping means for separating said liquid solute stream into a stripper overhead stream containing water and stripper bottoms stream containing sulfone and less than about 3 weight percent water.

9. A method as recited in claim 8 wherein said extract stream contains at least 70 weight percent of said sulfone of said hydrocarbon stream.

10. A method as recited in claim 9 wherein said hydrocarbon is a paraffin compound produced by the catalytic reaction of olefins and isoparaffin.

11. A method as recited in claim 10 wherein said sulfone is sulfolane.

12. A method as recited in claim 11 wherein the weight ratio of said solvent contacted with said hydrocarbon stream is at least about 0.01:1 solvent to hydrocarbon.

* * * * *

UNITED STATES PATENT AND TRADEMARK OFFICE
CERTIFICATE OF CORRECTION

PATENT NO. : 5,648,587

DATED : July 15, 1997

INVENTOR(S) : Keith W. Hovis and Richard L. Anderson

It is certified that error appears in the above-identified patent and that said Letters Patent is hereby corrected as shown below:

Column 8, claim 1, lines 54, delete "shipper" and insert --- stripper --- therefor.

Column 8, line 55 delete "shipping" and insert therefor --- stripping ---.

Column 8, line 55 delete "shipper" and insert therefor --- stripper ---.

Signed and Sealed this

Seventh Day of October, 1997

Attest:

BRUCE LEHMAN

Attesting Officer

Commissioner of Patents and Trademarks